(12) United States Patent
Wedam et al.

(10) Patent No.: US 12,232,950 B2
(45) Date of Patent: Feb. 25, 2025

(54) BONE ANCHOR INSERTION SYSTEM HAVING INSERTER COUPLING AND DECOUPLING

(71) Applicant: Acumed LLC, Hillsboro, OR (US)

(72) Inventors: Brandon Wedam, North Plains, OR (US); Travis Cox, North Plains, OR (US); Steven P. Horst, Dayton, OR (US); Tristan Sommers, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 208 days.

(21) Appl. No.: 17/516,205

(22) Filed: Nov. 1, 2021

(65) Prior Publication Data

US 2022/0133466 A1 May 5, 2022

Related U.S. Application Data

(60) Provisional application No. 63/108,672, filed on Nov. 2, 2020.

(51) Int. Cl.
*A61F 2/08* (2006.01)
(52) U.S. Cl.
CPC .......... *A61F 2/0811* (2013.01); *A61F 2/0805* (2013.01); *A61F 2002/0852* (2013.01);
(Continued)
(58) Field of Classification Search
CPC .................. A61F 2/0811; A61F 2/0805; A61F 2002/0852; A61F 2002/0882;
(Continued)

(56) References Cited

U.S. PATENT DOCUMENTS 5,749,899 A * 5/1998 Bardin ............... A61B 17/0401
606/198
6,146,406 A * 11/2000 Shluzas ............. A61B 17/0401
606/232
(Continued)

FOREIGN PATENT DOCUMENTS

CN 110418613 A 11/2019

OTHER PUBLICATIONS

International Preliminary Report corresponding to related International Patent Application No. PCT/US2021/057582, mailed May 11, 2023, 8 pages.

(Continued)

*Primary Examiner* — Javier G Blanco
(74) *Attorney, Agent, or Firm* — K&L Gates LLP

(57) ABSTRACT

Bone anchors and bone anchor insertion systems are provided that enable smaller bone holes for inserting a bone anchor by eliminating the need for a cannula. Smaller bone holes may help reduce patient recovery times. The provided bone anchor includes two flexible wings extending from a base portion that splay away from the base portion's central axis at rest, though may be bent towards or away from the central axis in response to an applied force. The bone anchor includes a drive feature that enables an inserter to couple and decouple to the bone anchor. A surgeon may drive the bone anchor through a bone hole via the coupled inserter while the bone hole maintains the bone anchor in a compressed state, and may decouple the inserter when the bone anchor is properly positioned, thereby eliminating the need for a cannula.

10 Claims, 4 Drawing Sheets

(52) U.S. Cl.
CPC ............... *A61F 2002/0882* (2013.01); *A61F 2210/0014* (2013.01); *A61F 2220/0033* (2013.01); *A61F 2230/0093* (2013.01)

(58) Field of Classification Search
CPC ...... A61F 2210/0014; A61F 2220/0033; A61F 2230/0093; A61B 17/0401; A61B 17/7266; A61B 2017/0437
See application file for complete search history.

(56) References Cited

U.S. PATENT DOCUMENTS

| | | | |
|---|---|---|---|
| 7,780,701 B1* | 8/2010 | Meridew | A61B 17/0401 606/232 |
| 8,753,372 B2 | 6/2014 | Petros | |
| 2003/0135225 A1* | 7/2003 | Harari | A61B 17/0401 606/151 |
| 2003/0233095 A1* | 12/2003 | Urbanski | A61F 2/0811 606/301 |
| 2009/0318964 A1* | 12/2009 | Lombardo | A61B 17/0401 606/232 |
| 2013/0274798 A1 | 10/2013 | Vyhmeister | |
| 2015/0073478 A1* | 3/2015 | Belson | A61B 17/0401 606/232 |
| 2017/0215867 A1* | 8/2017 | Arai | A61F 2/0811 |
| 2020/0146668 A1 | 5/2020 | Krumme | |

OTHER PUBLICATIONS

International Search Report corresponding to related International Patent Application No. PCT/US2021/057582 mailed Feb. 3, 2022, 3 pages.

International Written Opinion corresponding to related International Patent Application No. PCT/US2021/057582 mailed Feb. 3, 2022, 11 pages.

Extended European Search Report corresponding to related European Patent Application No. 21887725.6 dated Aug. 22, 2024, 15 pages.

* cited by examiner

BONE ANCHOR INSERTION SYSTEM HAVING INSERTER COUPLING AND DECOUPLING

PRIORITY CLAIM

The present application claims priority to and the benefit of U.S. Provisional Application 63/108,672, filed Nov. 2, 2020, the entirety of which is herein incorporated by reference.

BACKGROUND

Bone anchors are used extensively in open and minimally invasive surgery to reattach tissue to bone. The bone anchor is secured to the bone and one or more sutures attached to the bone anchor are used to secure the tissue to the bone. The tissue can be soft tissue anywhere in the body, for example, a torn rotator cuff in a shoulder or a torn ligament. Typically, in a first step to reattach tissue to bone, a hole is drilled into the bone under arthroscopic visualization. The bone anchor may be inserted through the hole and may be configured to lock itself within the hole in the bone upon deployment therein. Once the bone anchor is secured within the hole in the bone, one or both ends of suture attached to the bone anchor may be tensioned to approximate the positioning of the tissue with respect to the bone. Once the tissue is positioned as desired, the suture may be locked in place to maintain the tension in the suture. The free end or ends of the suture may be clipped under arthroscopic visualization to complete the procedure.

The bone hole size that is drilled when inserting the bone anchor corresponds in part to a patient's recovery time. Accordingly, a smaller bone hole size is desired to reduce recovery times for patients. A bone anchor, however, must have sufficient pull-out strength so that it stays in place and allows tissue to properly reattach to bone. Therefore, it is desired that a bone anchor is small enough to be inserted through a bone hole while also having reliable pull-out strength such that it is not pulled back through the bone hole.

One way to provide such bone anchor properties is a bone anchor having wings constructed with a shape-memory material. The bone anchor may be shape-set in an expanded state with the wings splayed outward, though may be compressed to a smaller size with the wings bent inward as it is translated through a bone hole. Once the bone anchor reaches softer bone (e.g., cancellous bone), the bone anchor returns to its expanded state. In its expanded state, the bone anchor cannot translate back through the bone hole (e.g., cortical bone) because the wings are splayed outward wider than the bone hole.

Typical shape-memory material bone anchors, however, must be inserted through a bone hole with the use of an inserter having a cannula, or may otherwise not have a drive feature that can be used with an inserter. For instances with an inserter having a cannula, the bone anchor is positioned within the cannula so that the cannula maintains the bone anchor in a compressed state as it is translated through the bone hole. The bone anchor can then be deployed from the cannula into its expanded state once a desired depth into the bone is reached. The cannula, however, necessitates a larger bone hole than if the bone anchor was inserted into the bone hole on its own, since the cannula surrounds the bone anchor. The larger bone hole may contribute to increased patient recovery times.

Accordingly, there is a need for a bone anchor and insertion system that solves the above drawbacks.

SUMMARY

The present disclosure provides a new and innovative bone anchor that includes a drive feature for coupling and decoupling the bone anchor to an inserter. The present disclosure additionally provides new and innovative bone anchor insertion systems that enable inserting a bone anchor through smaller bone holes than typical bone anchor insertion systems by eliminating the need for a cannula to insert the bone anchor.

In an example, a bone anchor insertion system includes an inserter and a bone anchor. The inserter includes a rod having an insertion tip. The insertion tip has a width greater than at least a portion of the rod. The bone anchor includes a base portion and two wings extending from the base portion. Each of the two wings at rest are splayed away from a central axis of the base portion and are configured to bend towards and away from the central axis. The two wings and the central axis are all in the same plane. Each wing includes a protrusion directed at least partially towards the central axis. The bone anchor is configured such that the respective protrusions of the wings couple the insertion tip to the bone anchor.

In another example, a bone anchor insertion system includes an inserter, a bone anchor, and suture. The inserter includes a rod having an insertion tip. The insertion tip has a width greater than at least a portion of the rod. The bone anchor includes a base portion and two wings extending from the base portion. Each of the two wings at rest are splayed away from a central axis of the base portion and are configured to bend towards and away from the central axis. The two wings and the central axis are all in the same plane. Each wing includes a protrusion directed at least partially towards the central axis. The suture is positioned through the opening of the base portion such that the suture is coupled to the bone anchor. The bone anchor is configured such that the respective protrusions of the wings couple the insertion tip to the bone anchor while the wings are at rest. Bending the wings a threshold amount away from the central axis enables the insertion tip to be released from the bone anchor.

In another example still, a bone anchor includes a base portion having an opening and two wings extending from the base portion. The bone anchor is constructed of a shape memory material. Each of the two wings are shape-set to splay away from a central axis of the base portion. The two wings are configured to bend towards and away from the central axis. The two wings and the central axis are all in the same plane. Each wing includes a protrusion directed at least partially towards the central axis.

DETAILED DESCRIPTION

Figure 1:
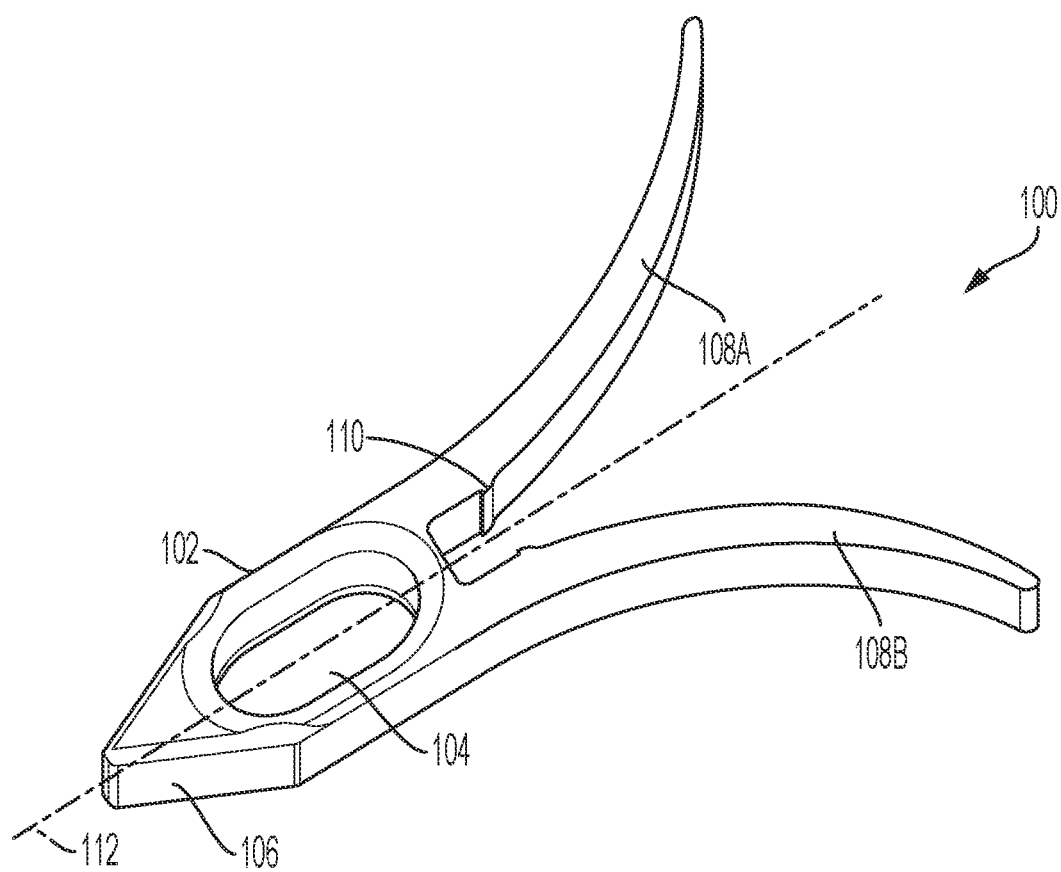
FIG. 1 illustrates a perspective view of a bone anchor, according to an aspect of the present disclosure.

The present disclosure provides new and innovative bone anchors and bone anchor insertion systems that enable smaller bone holes for inserting a bone anchor. The presently disclosed bone anchor includes two wings extending from a base portion. The two wings are in the same plane as a central axis of the base portion. At rest, the wings are splayed away from the base portion's central axis, though the wings may be bent towards or away from the central axis in response to an applied force. For instance, as the bone anchor is driven into a bone hole that is narrower than the outward perimeter of the splayed wings, the bone hole walls force the splayed wings to bend towards the base portion's central axis to a compressed state in order to fit within the bone hole. Once the force is insufficient to maintain the wings in the compressed state (e.g., softer bone), the wings return to their initial, splayed outward state. In an example, the bone anchor is constructed of a shape memory material that is shape-set so that the wings splay away from the base portion's central axis.

The provided bone anchor additionally includes a drive feature that enables a presently disclosed inserter to couple to the bone anchor. The inserter includes a rod having an insertion tip. The rod may be connected to a handle. A surgeon may drive the bone anchor through a bone hole via the coupled inserter. The drive feature includes a protrusion on each of the two wings. The protrusions are located on the wings such that the protrusions are at least partially directed towards the base portion's central axis (e.g., as the wings are bent, the directions of the protrusions change). The protrusions along with a portion of each wing and the base portion form an area that matches a shape of the insertion tip of the presently disclosed inserter. The insertion tip may be positioned within this area while the protrusions prevent the insertion tip from being removed from the bone anchor along the base portion's central axis. The inserter, in effect, is coupled to the bone anchor. The presently disclosed bone anchor insertion system may also include suture that is positioned through an opening in the bone anchor's base portion. The suture is used to lock the bone anchor in place to secure tissue to bone.

When the wings are bent towards the base portion's central axis while the bone anchor is coupled to the inserter, additional force is applied to the inserter by the wings (e.g., the protrusions) as compared to the bone anchor being at rest. For example, the wings are bent towards the base portion's central axis when the bone anchor is being driven through a bone hole. The additional force applied to the inserter by the wings increases a coupling strength of the bone anchor to the inserter. Conversely, when the wings are bent away from the base portion's central axis a sufficient amount, the space between the protrusions widens enough such that the insertion tip may be removed from the bone anchor along the base portion's central axis.

Accordingly, a surgeon may drive the provided bone anchor via the provided inserter through a bone hole (e.g., in cortical bone) that maintains the wings in a compressed state, bent towards the base portion's central axis. For instance, cortical bone has a sufficient hardness to maintain the bone anchor in its compressed state. The coupling strength of the bone anchor to the inserter is additionally increased while the bone anchor is within the bone hole. Once the bone anchor reaches softer bone (e.g., cancellous bone), the wings expand back to their resting state. As the inserter is removed from the bone hole, the bone anchor's wings are forced towards the harder bone (e.g., cortical bone), which causes the wings to bend away from the base portion's central axis. As the wings bend away, the distance between the protrusions widens, and the inserter is released from the bone anchor.

As compared to typical bone anchor insertion systems, a cannula is not needed to transport the provided bone anchor. Moreover, a cannula is not needed to maintain the provided bone anchor in a compressed state. Rather, while the surgeon drives the bone anchor through the bone hole, the bone anchor is maintained in a compressed state by the bone hole itself. Accordingly, smaller bone holes may be drilled by eliminating the need for an inserter with a cannula to deploy a bone anchor, which may help contribute to decreased patient recovery times.

Figure 2:
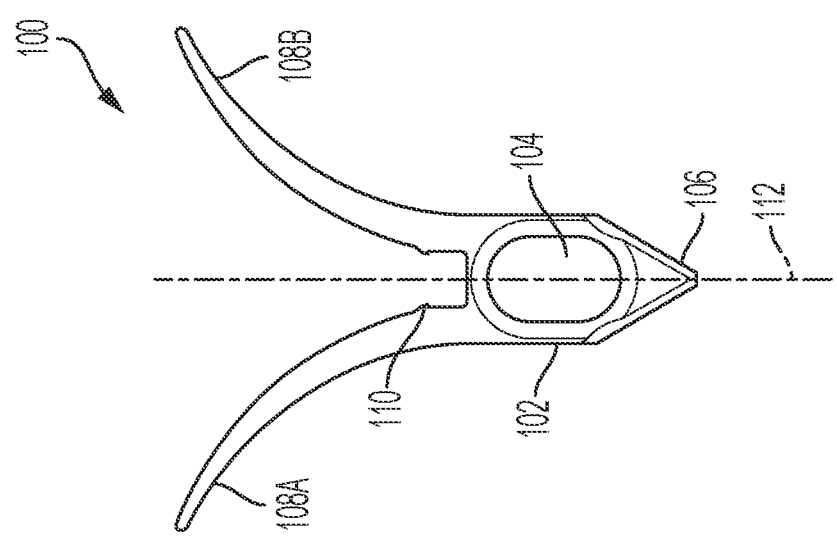
FIG. 2 illustrates a side view of a bone anchor, according to an aspect of the present disclosure.

FIGS. 1 and 2 illustrate a perspective view and side view, respectively, of an example bone anchor 100. The example bone anchor 100 includes a base portion 102. The base portion 102 may include an opening 104. In some aspects, the base portion 102 may include a dull, pointed tip 106. The pointed nature of the tip 106 helps the bone anchor 102 drive through tissue and into soft bone (e.g., cancellous bone). The dull nature of the tip 106 helps prevent accidental damage to tissue or bone.

Opposite the tip 106, two flexible wings 108A and 108B extend from the base portion 102. The flexible wings 108A and 108B in a rest position each splay away from a central axis 112 of the base portion 102. For instance, the bone anchor 100 may be constructed of a shape-memory material and the flexible wings 108A and 108B may be shape-set to splay away from the central axis 112. The flexible wings 108A and 108B may bend towards the central axis 112 in response to an applied force. For instance, the flexible wings 108A and 108B may bend such that they are substantially parallel with the central axis 112. The flexible wings 108A and 108B may also bend away from the central axis 112 in response to an applied force, further splaying away from the central axis 112. In either instance, when the applied force is removed, the wings 108A and 108B return to the illustrated rest position.

The flexible wings 108A and 108B may have a length that is longer than the base portion 102, such as in the illustrated example. In various aspects, the flexible wing 108A and the flexible wing 108B may have equal lengths. In such aspects, the bone anchor 100 may be symmetrical about the central axis 112. In other aspects, the flexible wing 108A and the flexible wing 108B may have unequal lengths. In some instances, the flexible wing 108A and the flexible wing 108B may be splayed away from the central axis 112 different amounts in the rest position.

Each of the wings 108A and 108B includes a protrusion 110. Only the protrusion 110 of the wing 108A is indicated solely for illustrative purposes. As illustrated, the protrusions 110 are located on the wings 108A, 108B such that they are directed at least partially towards the central axis 112. The direction of the protrusions 110 changes as the wings 108A, 108B are bent towards or away from the central axis 112.

Figure 3:
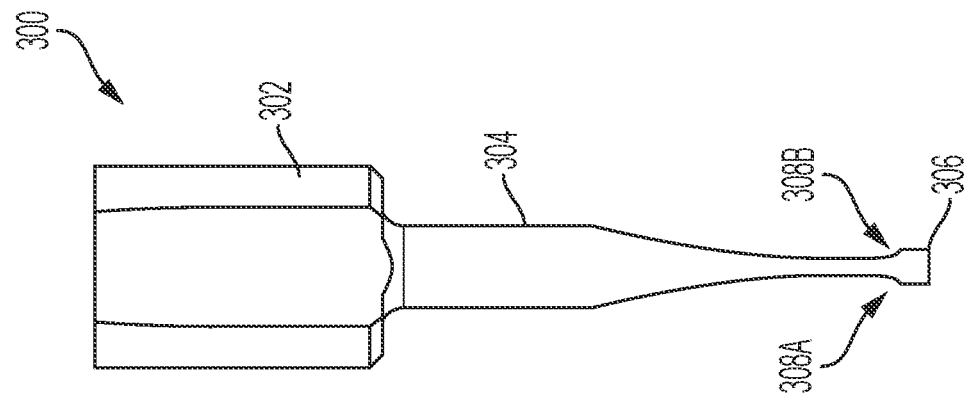
FIG. 3 illustrates a side view of an inserter, according to an aspect of the present disclosure.

FIG. 3 illustrates a side view of an example inserter 300. The inserter 300 may be used with the bone anchor 100. The inserter 300 includes a rod 304 with an insertion tip 306. The rod 304 includes a recess 308A and 308B on opposing sides of the rod 304. The recesses 308A, 308B are adjacent to the insertion tip 306. Due to the recesses 308A and 308B, the insertion tip 306 has a width greater than at least the portion of the rod 304 directly adjacent to the insertion tip 306. Setting off the insertion tip 306 from at least a portion of the rod 304 enables the insertion tip 306 to be coupled to the example bone anchor 100, which will be discussed more below. The example inserter 300 may include a handle 302 removably or fixedly connected to the rod 304.

Figure 4:
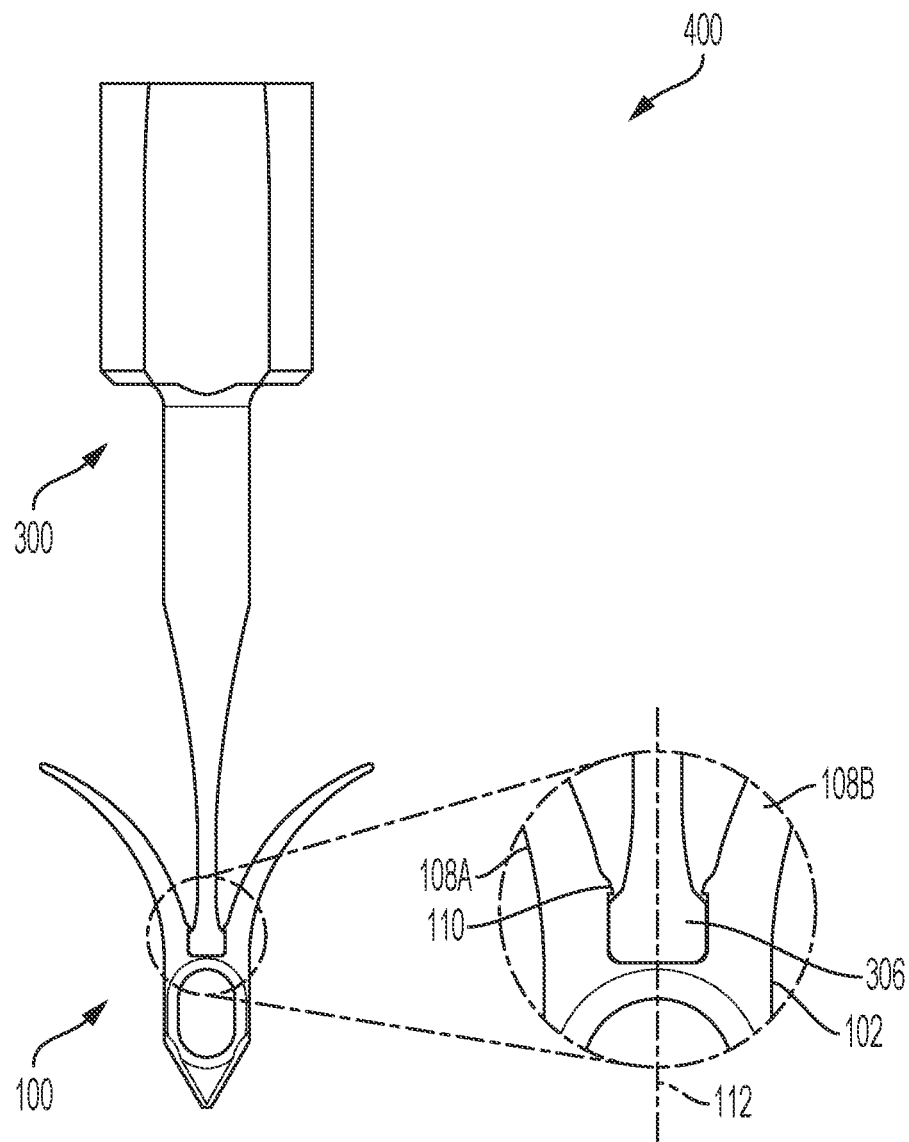
FIG. 4 illustrates a side view of a bone anchor insertion system including an inserter coupled to a bone anchor, according to an aspect of the present disclosure.

FIG. 4 illustrates a side view of an example bone anchor insertion system 400. The bone anchor insertion system 400 includes the example inserter 300 and the example bone anchor 100. The bone anchor 100 includes a drive feature that enables a surgeon to couple the inserter 300 to the bone anchor 100 and drive the bone anchor 100 through a bone hole. The drive feature also enables the surgeon to decouple the inserter 300 from the bone anchor 100.

A magnified image of the drive feature is shown in FIG. 4 to better illustrate how the inserter 300 couples to the bone anchor 100. A profile formed by the protrusions 110, a portion of each flexible wing 108A, 108B, and the base portion 102 of the bone anchor 100 matches a profile of the insertion tip 306 such that the insertion tip 306 form fits within the space created by the bone anchor 100 profile. The protrusions 110 maintain the insertion tip 306 within this space and prevent the insertion tip 306 from translating away from the bone anchor 100 along the central axis 112, thereby coupling the inserter 300 to the bone anchor 100.

To position the insertion tip 306 within the space created by the bone anchor 100 profile, the insertion tip 306 may be translated along the central axis 112 until the insertion tip 306 snaps into place. Stated differently, the flexible wings 108A, 108B splay further away from the central axis 112 to enable the insertion tip 306 to pass between the protrusions 110, and then return to their resting position. Alternatively, the insertion tip 306 may be slid into the space from the side (e.g., perpendicular to the central axis 112). As the flexible wings 108A and 108B are bent away from the central axis 112, the distance between the protrusions 110 increases. When such distance is greater than the width of the insertion tip 306, the protrusions 110 no longer prevent the insertion tip 306 from translating along the central axis 112, thus enabling the inserter 300 to decouple from the bone anchor 100.

The bone anchor insertion system 400 may further include suture. The suture may be positioned through the opening 104 of the bone anchor 100 to couple the suture to the bone anchor 100. The suture may also be coupled to the inserter 300 during insertion of the bone anchor 100. Once the bone anchor 100 is inserted, the suture may be released from the inserter 300 and may be used in conjunction with the bone anchor 100 to secure tissue to bone.

Figure 5C:
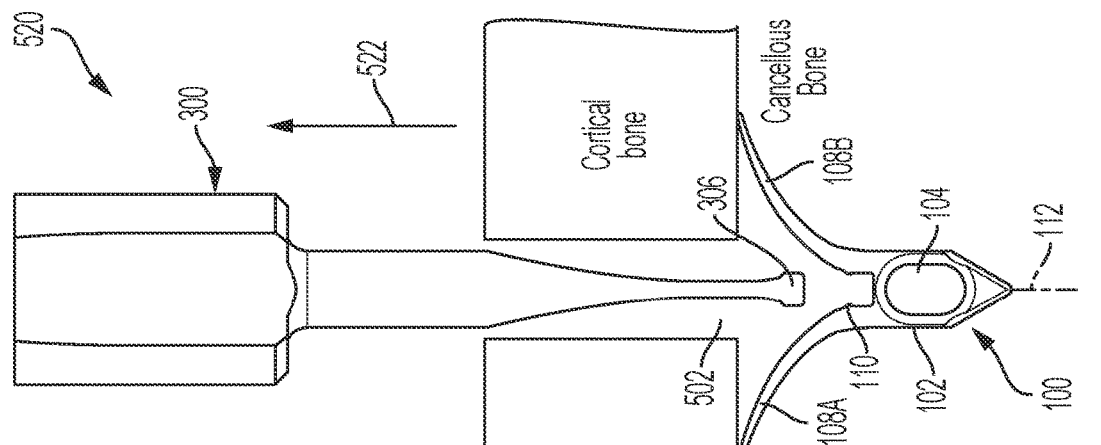
FIGS. 5A to 5C illustrate side views of a method for inserting a bone anchor with a bone anchor insertion system, according to an aspect of the present disclosure.
Figure 5B:
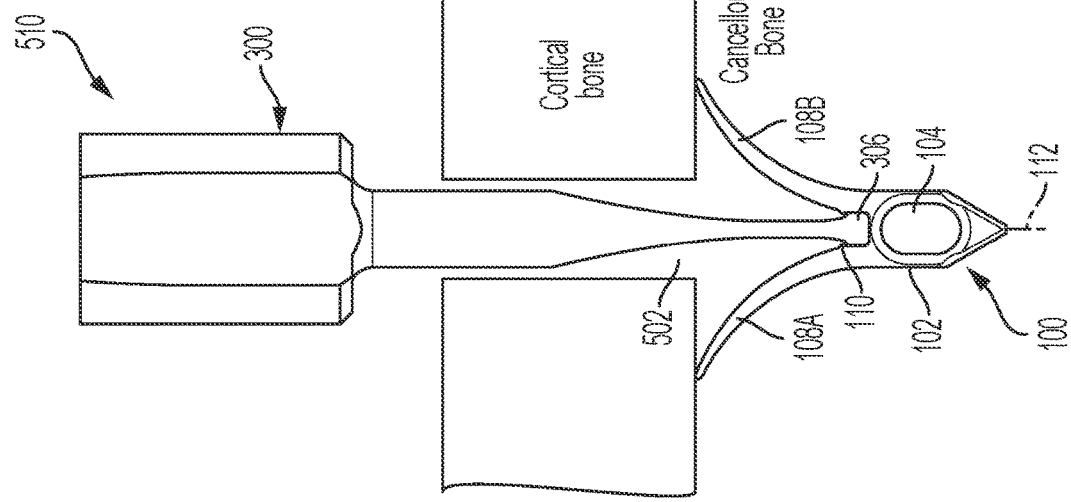
Figure 5A:
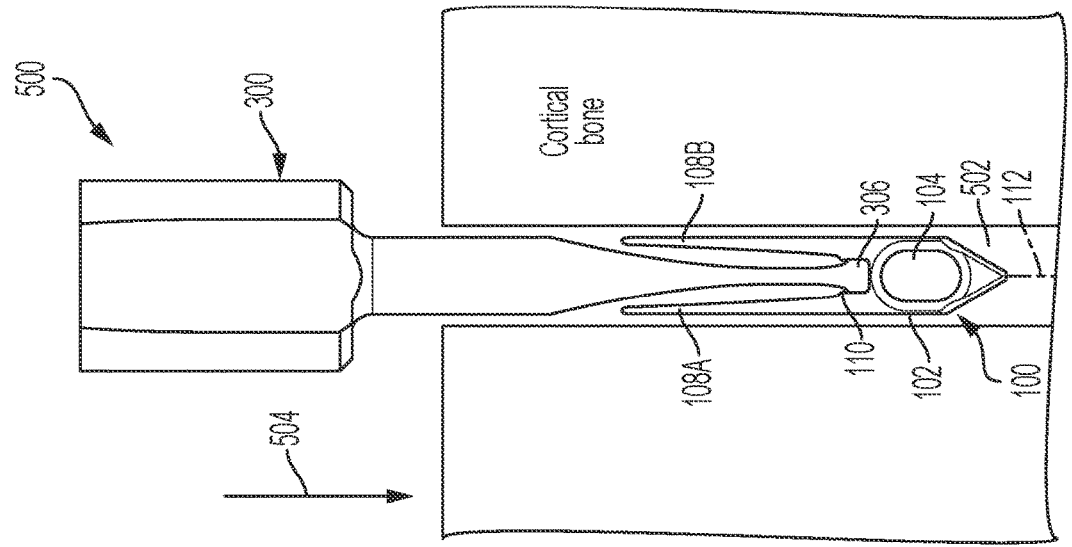

FIGS. 5A to 5C illustrate side views of example processes for inserting the bone anchor 100 using the inserter 300. While suture is not illustrated in the figures, suture may be coupled to the bone anchor 100 through the opening 104. The example process 500 of FIG. 5A illustrates the inserter 300 coupled to the bone anchor 100 as a surgeon drives the bone anchor 100 through a bone hole 502 in the direction of the arrow 504. The bone hole 502 may be created by drilling into cortical bone. In some instances, the bone hole 502 may extend into cancellous bone. In other instances, the bone hole 502 is created in cortical bone only. In such other instances, the bone anchor 100 may be driven into the cancellous bone. A gap is illustrated between the walls of the bone hole 502 and the bone anchor 100 solely for the sake of clarity. As the surgeon drives the bone anchor 100 into and through the bone hole 502, the outer surface of the bone anchor 100 contacts the walls of the bone hole 502, which causes the flexible wings 108A and 108B to fold up or bend towards the central axis 112 as illustrated. The hardness of cortical bone is sufficient to effect an opposing force that maintains the flexible wings 108A and 108B in this folded up or compressed state.

In some instances, such as the illustrated example, once the surgeon drives the bone anchor 100 into softer bone, such as cancellous bone, the hardness of the cancellous bone is insufficient to effect such an opposing force. The flexible wings 108A and 108B accordingly splay away from the central axis 112, into the cancellous bone, to return to their resting position, as illustrated in the example process 510 of FIG. 5B. At this stage, the protrusions 110 still couple the insertion tip 306 to the bone anchor 100. In other instances, the softer bone, such as cancellous bone, has a hardness that is sufficient to effect an opposing force that maintains the flexible wings 108A and 108B in its compressed state, or at least prevents the flexible wings 108A and 108B from fully returning to their resting position. In such other instances, the flexible wings 108A and 108B are at least partially compressed towards one another at this stage in the example process (e.g., in FIG. 5B).

The example process 520 of FIG. 5C illustrates a surgeon removing the inserter 300 from the bone hole 502 in the direction of the arrow 522. As the surgeon translates the inserter 300 in the direction of the arrow 522, the base portion 102 of the bone anchor 100 moves with the inserter 300 since the bone anchor 100 remains coupled to the inserter 300. The flexible wings 108A and 108B, however, are prevented from translating in the direction of the arrow 522 by the cortical bone. Instead, the cortical bone causes the flexible wings 108A and 108B to splay or bend away from the central axis 112. Once the flexible wings 108A and 108B splay or bend apart a sufficient amount, the distance between the protrusions 110 is great enough to allow the insertion tip 306 to pass through. The inserter 300 is thereby decoupled from the bone anchor 100. Tension in the suture may then maintain the bone anchor 100 in this positioning. Removing the inserter 300 causes the flexible wings 108A and 108B to splay or bend away from the central axis 112 and release the inserter 300 whether or not the softer bone (e.g., cancellous bone) is soft enough to enable the flexible wings 108A and 108B to bend away from one other. For example, removing the inserter 300 in the direction of the arrow 522 may cause the flexible wings 108A and 108B to bend away from another and release the inserter 300 all in one motion.

The presently disclosed bone anchor insertion system therefore enables smaller bone holes as compared to typical bone anchor insertion systems by eliminating the need for a cannula to transport a bone anchor. Rather than a cannula, the presently disclosed bone anchor insertion system includes a bone anchor with a drive feature that enables a surgeon to couple an inserter to the bone anchor and use the inserter to drive the bone anchor through a bone hole, which maintains the bone anchor in a folded up or compressed state (e.g., FIG. 5A). The drive feature additionally enables the surgeon to decouple the inserter from the bone anchor (e.g., FIG. 5C).

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A bone anchor insertion system comprising:
   an inserter including a rod having an insertion tip and a first recess and a second recess adjacent to the insertion tip, wherein the insertion tip has a width greater than at least a portion of the rod; and
   a bone anchor including:
      a planar base portion comprising a distal end ending in a tip, a proximal end, and a transverse opening sized and configured to receive a suture therein,
      first and second elongated wings extending from the base portion, wherein the first and second elongated wings are configured to bend towards and away from a central axis of the base portion, wherein the first and second elongated wings, the base portion, and the central axis are all in the same plane, and
      a suture positioned through the opening of the base portion such that the suture is coupled to the bone anchor,
   wherein the bone anchor is constructed of a shape memory material,
   wherein each of the first and second elongated wings includes a protrusion directed at least partially towards the central axis, and wherein a distance between the protrusion of each wing increases when the first and second elongated wings are bent away from the central axis,
   wherein the first wing comprises:
      a first free end disposed at a distal most end of the first wing; and
      a first fixed end opposite the first free end, wherein the first fixed end is disposed at a proximal most end of the first wing and connected to the proximal end of the base portion,
   wherein the second wing comprises:
      a second free end disposed at a distal most end of the second wing; and
      a second fixed end opposite the second free end, wherein the second fixed end is disposed at a proximal most end of the second wing and connected to the proximal end of the base portion,
   wherein the protrusions of the first and second wings are disposed at proximal portions of the first and second wings, respectively,
   wherein the first free end of first wing and the second free end of the second wing are splayed away from the central axis of the base portion at a rest position,
   wherein the bone anchor is configured such that the respective protrusions of the first and second elongated wings couple the insertion tip to the bone anchor,
   wherein the protrusion of each wing is configured to engage the first recess and the second recess of the inserter, respectively, when the bone anchor is at rest to prevent translation of the inserter away from the bone anchor along the central axis,
   wherein bending the first and second elongated wings towards the central axis increases a coupling strength of the bone anchor to the inserter,
   wherein the bone anchor is configured such that bending the wings away from the central axis a threshold amount enables the insertion tip to decouple from the bone anchor.

2. The bone anchor insertion system of claim 1, wherein a profile formed by a portion of each wing, the base portion, and the respective protrusions of each wing has a first shape and a profile of the insertion tip has a second shape, wherein the first shape is the same as the second shape.

3. The bone anchor insertion system of claim 1, wherein the shape memory material is nitinol.

4. The bone anchor insertion system of claim 1, wherein the insertion tip is configured to be coupled to the bone anchor by translating the insertion tip along an axis perpendicular to the central axis until the insertion tip is between the first and second elongated wings.

5. The bone anchor insertion system of claim 1, wherein the bone anchor is symmetrical about the central axis.

6. The bone anchor insertion system of claim 1, wherein the first and second elongated wings have equal lengths.

7. The bone anchor insertion system of claim 1, wherein the bone anchor is configured such that opposing cortical bone surfaces maintain the first and second elongated wings in a position bent towards the central axis as compared to the first and second elongated wings at rest.

8. The bone anchor insertion system of claim 1, wherein the bone anchor is configured such that opposing cancellous bone surfaces maintain the first and second elongated wings in a position bent towards the central axis as compared to the first and second elongated wings at rest.

9. The bone anchor insertion system of claim 1, wherein the bone anchor is configured to be driven through a bone canal via the inserter without the use of a cannula.

10. The bone anchor insertion system of claim 1, wherein the first and second elongated wings have a length longer than the base portion.

* * * * *